May 5, 1959 J. GAUJARD Plant Pat. 1,829
ROSE PLANT
Filed Sept. 24, 1958
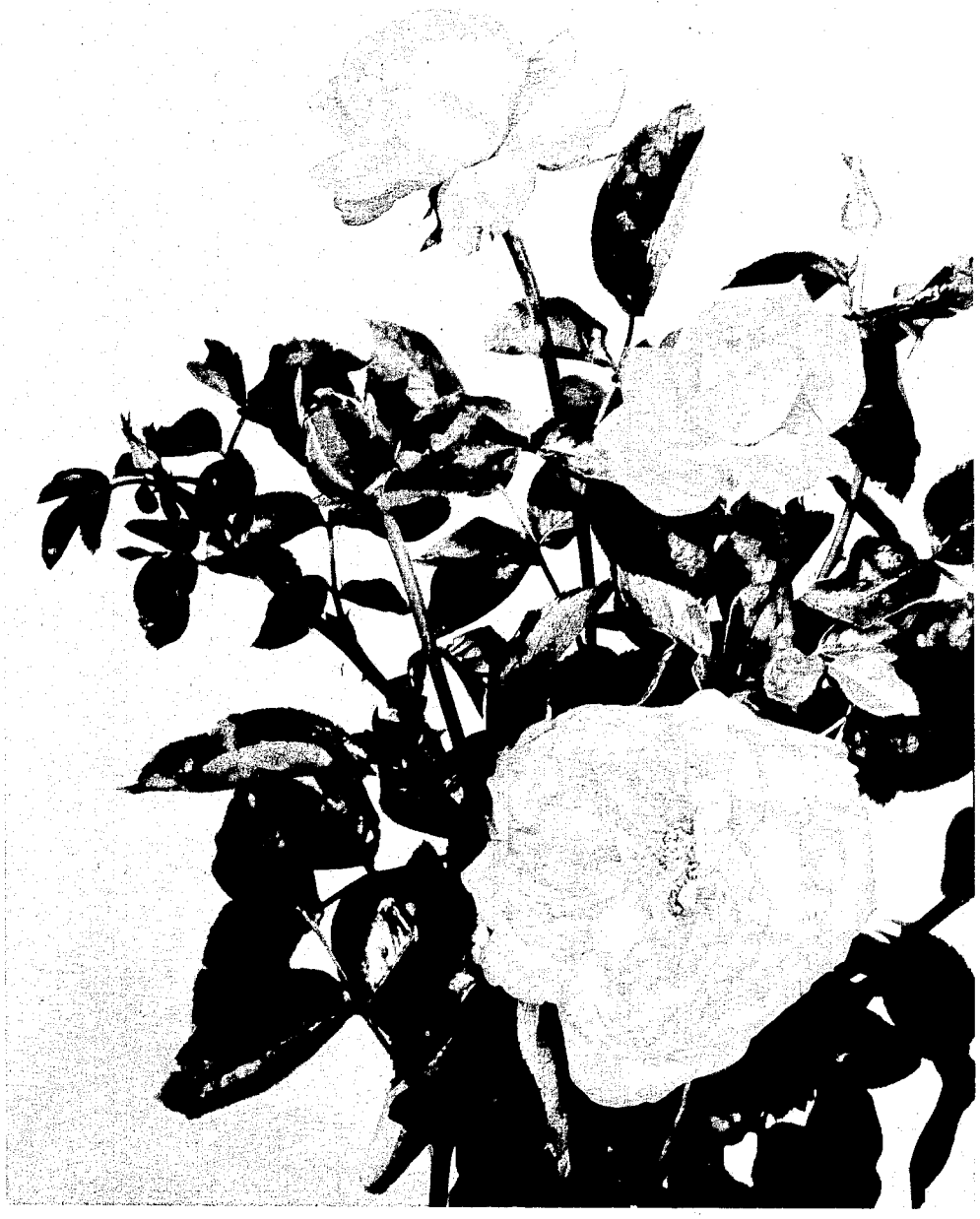
Inventor.
Jean Gaujard
By: Robert Robb
Attorneys.

United States Patent Office

Plant Pat. 1,829
Patented May 5, 1959

1,829

ROSE PLANT

Jean Gaujard, Feyzin, France, assignor to Armstrong Nurseries, Inc., Ontario, Calif., a corporation of California Application September 24, 1958, Serial No. 763,151

Claims priority, application France September 26, 1957

1 Claim. (Cl. 47—61)

The present invention relates to a new and distinct variety of rose plant of the hybrid tea class, which was originated by me by crossing the variety "Peace" (U.S. Plant Patent No. 591) with an unnamed and unpatented seedling of "Capucine Bicolore" (unpatented) × "Opera" (U.S. Plant Patent No. 1,017), said unnamed seedling parent being particularly characterized by its brilliant plain red colored flowers and dark green foliage.

The primary objective of this breeding was to produce a new rose variety which bears flowers of a brilliant red color, combined with the over-all excellent flower qualities of the parent variety "Peace." This objective was fully achieved, along with other desirable improvements, as evidenced by the following unique combination of characteristics which are outstanding in the new variety and distinguish it from its parents, as well as from all other varieties of which I am aware:

(1) A vigorous, upright-spreading plant habit;

(2) Attractive, very glossy, leathery, dark green foliage;

(3) A floriferousness which is better-than-average for hybrid tea roses;

(4) Flowers of medium size which are borne usually singly on stems of medium length;

(5) Attractive, well-formed, high-centered, very double flowers; and (6) A brilliant red general color tonality of the flowers, ranging between Cherry and Rose Red, with the reverse of the flower petals generally ranging between pale pink and white, variably fringed and marked with red or pink and presenting an unusual contrast of colors, particularly in the partially open flower stage.

In comparison with its seed parent, "Peace," my new variety is more floriferous, but has a somewhat shorter average flower stem length; the flower size of the new variety is less than that of this parent; the petalage is greater; and the flower color is quite different in generally ranging between Cherry and Rose Red, with the reverse of the petals light pink or near white and having variable pink and red markings, while the flower colors of "Peace" are generally light yellow, with pink toward the petal margins.

As compared with its unnamed pollen parent, the foliage of my new variety is more leathery and glossy, and its flower color is quite different from the brilliant, plain red flower color of this parent.

Asexual reproduction of the new variety by budding, as performed in France, and also at Ontario, California, U.S.A., shows that the aforementioned characteristics and distinctions come true to form and are established and tansmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), except where general color terms of ordinary dictionary significance are obvious:

Type: Bush; seedling; for cut flowers and for garden decoration.

Class: Hybrid tea.

Breeding: Seedling.

*Seed parent.*—"Peace."

*Pollen parent.*—An unnamed seedling of "Capucine Bicolore" × "Opera."

Propagation: Holds its distinguishing characteristics through succeeding propagations by budding.

*Flower*

Locality where grown and observed: Ontario, California, U.S.A.

Flowers borne: Usually singly, but sometimes 3 or 4 to stem; in irregular clusters; on stems of medium length and from normal strength to strong.

Quantity of bloom: Abundant, outdoors.

Continuity: Nearly continuous during growing season.

Fragrance: From none to slight.

Bud:

*Peduncle.*—From average length to long; average caliper; erect; usually smooth; with from few to several small stipitate glands. Color—near Dark Olive Buff, Plate XL (Ridgway), overlaid with near Ocher Red, Plate XXVII (Ridgway) on side exposed to the sun.

*Before calyx breaks.*—Size—from small to medium. Form—from short to medium length; from ovoid to globular.

*As calyx breaks.*—Color—near Chrysanthemum Crimson, Plate 824/1, page 169 (Wilson), with near Indian Lake, Plate 826, page 170 (Wilson) on areas of petal that have been exposed longer to sun.

*Sepals.*—Inner surface—lined with fine, woolly tomentum. Outer surface—usually smooth; margins of alternate sepals lined with fine, woolly tomentum; margins of others usually lined with from few to several small stipitate glands and slender foliaceous appendages; sometimes foliaceous parts on tips of sepals extending to ⅓ of its length.

*As first petal opens.*—Size—from small to average. Form—short; broadly obovate. Color: outside—near Chrysanthemum Crimson, Plate 824/3, page 169 (Wilson), with near Chrysanthemum Crimson, Plate 824/1, page 169 (Wilson) on areas exposed longer to sun, and with small area at base near attachment near Uranium Green, Plate 63/2, page 63 (Wilson); inside—near Cardinal Red, Plate 822/3, page 168 (Wilson), with small area at base near attachment near Uranium Green, Plate 63/2, page 63 (Wilson).

*Opening.*—Opens up well; is not retarded from opening by cold, hot, wet or dry weather.

Bloom:

*Size (when open).*—Average; from 3 inches to 4 inches.

*Petalage.*—Very double; from 80 to 90 petals, with from 18 to 24 petaloids; arranged irregularly.

*Form.*—From high-centered to globular at first, but becoming cupped to high-centered; petals being at first tightly cupped, with tips reflexed outward, but later becoming more loosely cupped, with tips reflexed outward, at maturity.

Petals:

*Texture.*—Medium thickness; moderately soft. Inside—slightly velvety. Outside—slightly satiny.

*Shape.*—Outside—broadly obovate, with apex flat, and sometimes with from 1 to 3 notches. Intermediate—obovate, with apex rounded, and sometimes with 1 or 2 notches. Inside—obovate, with apex rounded.

This description of a newly opened flower was made from a rose grown outdoors in the month of August at Ontario, California, U.S.A.:

*Color.*—Outer petal: outside surface—between Cherry, Plate 722/3, page 157 (Wilson) and Rose Red, Plate 724/3, page 158 (Wilson), with markings of near Uranium Green, Plate 63/3, page 63 (Wilson) running from base toward outer margins, and with small area near attachment near Uranium Green, Plate 63/2, page 63 (Wilson); inside surface—between Cherry, Plate 722/2, page 157 (Wilson) and Rose Red, Plate 724/2, page 158 (Wilson), blending into and mottled with near Crimson, Plate 22/3, page 22 (Wilson) toward base, and with area near attachment near Uranium Green, Plate 63/2, page 63 (Wilson). Intermediate petal: outside surface—near Rose Madder, Plate 23/3, page 23 (Wilson), with slight markings of near Rose Red, Plate 724/3, page 158 (Wilson), and with small area near attachment near Uranium Green, Plate 63/2, page 63 (Wilson); inside surface—near Rose Red, Plate 724/1, page 158 (Wilson), blending with near Rose Madder, Plate 23/3, page 23 (Wilson) toward base, and with area near attachment near Uranium Green, Plate 63/2, page 63 (Wilson). Inner petal: outside surface—near Rose Madder, Plate 23/3, page 23 (Wilson), with slight markings of near Rose Red, Plate 724/2, page 158 (Wilson), and with small area near attachment near Uranium Green, Plate 63/2, page 63 (Wilson); inside surface—near rose Red, Plate 724, page 158 (Wilson), blending with near Rose Madder, Plate 23/2, page 23 (Wilson) toward base, and with area near attachment near Uranium Green, Plate 63/2, page 63 (Wilson).

This description was made from a rose that was open for 3 days outdoors in the month of August at Ontario, California, U.S.A.:

*Color.*—Outer petal: outside surface—near Tyrian Rose, Plate 24/3, page 24 (Wilson), with markings of near Tyrian Rose, Plate 24/1, page 24 (Wilson) near outer margin, and blending toward base into near Dresden Yellow, Plate 64/3, page 64 (Wilson); inside surface—near Tyrian Rose, Plate 24/1, page 24 (Wilson), fading irregularly to near Rose Bengal, Plate 25/3, page 25 (Wilson), and becoming toward base near Dresden Yellow, Plate 64/3, page 64 (Wilson). Inner petal: outside surface—between White and near Tyrian Rose, Plate 24/3, page 24 (Wilson), with few markings of near Tyrian Rose, Plate 24/1, page 24 (Wilson) near outer margin, blending toward base into between White and near Dresden Yellow, Plate 64/3, page 64 (Wilson), and with small area at base near attachment near Dresden Yellow, Plate 64/3, page 64 (Wilson); inside surface—near Tyrian Rose, Plate 24, page 24 (Wilson), fading irregularly to near Rose Bengal, Plate 25/2, page 25 (Wilson) and near Rose Bengal, Plate 25/3, page 25 (Wilson), and becoming toward base near Dresden Yellow, Plate 64/3, page 64 (Wilson).

*General color effect.*—Newly opened flower—between Cherry, Plate 722/3, page 157 (Wilson) and Rose Red, Plate 724/1, page 158 (Wilson). 3-days open—between Tyrian Rose, Plate 24/1, page 24 (Wilson) and Rose Bengal, Plate 25/2, page 25 (Wilson).

*Behavior.*—Drop off cleanly; not particularly affected by cold, hot, wet or dry weather.

*Flower longevity.*—On bush in garden—4 or 5 days in August. Cut roses grown outdoors and kept at living-room temperatures—4 or 5 days in August.

*Reproductive organs*

*Stamens*: Average number; arranged regularly about pistils; a few mixed with petaloids.

*Filaments*: From short to medium length; from 3 mm. to 10 mm. in length; most with anthers. Color—near Crimson, Plate 22/1, page 22 (Wilson).

*Anthers*: From small to medium size; all open approximately at once. Color: upper side—margins near Yellow Ochre, Plate 07/1, page 101 (Wilson), with remainder near Aureolin, Plate 3/3, page 3 (Wilson); under side—margins near Yellow Ochre, Plate 07/1, page 101 (Wilson), with remainder near Aureolin, Plate 3/3, page 3 (Wilson).

Pollen: From moderate to abundant. Color—near Cadmium Orange, Plate 8, page 8 (Wilson).

Pistils: Many; approximately 90 in number.

Styles: Uneven; from short to average length; from 4 mm. to 10 mm. in length; from thin to average caliper; bunched. Color—upper ⅓ of style near Azalea Pink, Plate 618/3, page 74 (Wilson), with remainder near Empire Yellow, Plate 603/3, page 66 (Wilson).

Stigma: Color—near Indian Yellow, Plate 6/2, page 6 (Wilson).

Ovaries: Usually all enclosed in calyx.

Hips: None observed.

Sepals: None observed.

Seeds: None observed.

*Plant*

Foliage:

*Leaves.*—Compound of usually 3 to 7 leaflets; from normal quantity to abundant; from medium size to large; leathery; very glossy.

*Leaflets.*—Shape—between oval and oblong, with apex acute. Base—round. Margin—usually doubly serrate.

*Color.* — Mature: upper surface — between Bice Green, Plate XVII (Ridgway) and Deep Dull Yellow-Green (1), Plate XXXII (Ridgway); under surface—near Asphodel Green, Plate XLI (Ridgway). Young: upper surface—between Buffy Olive, Plate XXX (Ridgway) and Olive Brown, Plate XL (Ridgway); under surface—near Sorghum Brown, Plate XXXIX (Ridgway).

*Rachis (the supporting stem of the compound leaf).*—Average size. Upper side—grooved; with from few to several small stipitate glands on edges. Under side—usually smooth, with from none to few small prickles.

*Stipules.*—From short to medium length; medium width; with from short to medium length points turning out at an angle of approximately 45°.

*Disease resistance.*—Average resistance to mildew, as compared with other varieties grown under comparable cultural conditions at Ontario, California, U.S.A.

Growth:

*Habit.*—Bushy; upright-spreading; much-branched.

*Growth.*—Vigorous.

*Canes.*—From medium caliper to heavy.

*Main stems.*—Color—between Rainette Green, Plate XXXI (Ridgway) and Light Cress Green, Plate XXXI (Ridgway). Large prickles—from few to several; from medium length to long; hooked slightly downward; with from short to medium length and moderately narrow base; color—near Cinnamon, Plate XXIX (Ridgway). Small prickles—from none to few; color—near Cinnamon, Plate XXIX (Ridgway). Hairs—none.

*Branches.*—Color—near Chromium Green, Plate XXXII (Ridgway). Large prickles—several; from medium length to long; hooked slightly downward; with medium length, moderately narrow base; color—between Walnut Brown, Plate XXVIII (Ridgway) and Rood's Brown, Plate XXVIII (Ridgway). Small prickles—from none to few; color—between Walnut Brown, Plate XXVIII (Ridgway) and Rood's Brown, Plate XXVIII (Ridgway). Hairs—none.

*New shoots.*—Color—near Ecru Olive, Plate XXX (Ridgway), overlaid with near Walnut Brown, Plate XXVIII (Ridgway) on side exposed to sun. Large prickles—few; medium length; hooked slightly downward; with medium length, narrow base; color—near Hydrangea Red, Plate XXVII (Ridgway). Small prickles—few; color—near Hydrangea Red, Plate XXVII (Ridgway). Hairs—none.

I claim:

A new and distinct variety of rose plant of the hybrid tea class, substantially as herein shown and described, characterized particularly as to novelty by the unique combination of a vigorous and upright-spreading plant habit, attractive, very glossy, leathery, dark green foliage, attractive, well-formed, high-centered, very double flowers of medium size borne usually singly on stems of medium length, a better-than-average floriferousness as compared with other hybrid tea roses, and a general brilliant red flower color tonality ranging between Cherry and Rose Red, with the reverse of the flower petals generally ranging in color between pale pink and white, variably fringed and marked with red or pink and presenting an unusual color contrast, particularly in the partially open flower stage.

No references cited.